US00PP12890P2

(12) United States Plant Patent
van Geest

(10) Patent No.: US PP12,890 P2
(45) Date of Patent: Aug. 27, 2002

(54) FICUS PLANT NAMED 'ECLIPSE'

(75) Inventor: Jan van Geest, s'Gravnezande (NL)

(73) Assignee: Plantenwekerij J. Van Geest, B.V., s'Gravnezande (NL)

( * ) Notice: Subject to any disclaimer, the term of this patent is extended or adjusted under 35 U.S.C. 154(b) by 31 days.

(21) Appl. No.: 09/661,159

(22) Filed: Sep. 13, 2000

(51) Int. Cl.[7] ..... A01H 5/00
(52) U.S. Cl. ..... Plt./211
(58) Field of Search ..... Plt./211

(56) References Cited

PUBLICATIONS

UPOV–ROM GTITM Computer Database, 2001/02, GTI Jouve Retrieval Software, citation for 'Eclipse'.*

European Union application No. 98/1040 for Community Plant Variety Right, Jul. 28, 1998.

* cited by examiner

*Primary Examiner*—Bruce R. Campell
*Assistant Examiner*—Susan B. McCormick
(74) *Attorney, Agent, or Firm*—Foley & Lardner

(57) ABSTRACT

A new and distinct variety of *Ficus benjamina* designated 'Eclipse' particularly characterized by dark green foliage that is elliptic with an exaggerated acuminate leaf tip with crenate undulating leaf margins. The leaves are glossy on both sides and the plant has a somewhat weeping growth habit with irregular branching.

2 Drawing Sheets

BACKGROUND OF THE INVENTION

The present invention relates to a new and distinct cultivar of *Ficus benjamina*. The varietal denomination of the new cultivar is 'Eclipse'. The new variety was discovered as a mutation in a controlled planting of *Ficus benjamina* 'Midnight' in a greenhouse in s'Gravenzande, The Netherlands in January 1995.

SUMMARY OF THE INVENTION

The new variety is a naturally-occurring mutation of the Ficus variety 'Midnight' (U.S. Plant Pat. No. 9,856). The new variety was discovered by the inventor Jan van Geest in a greenhouse in s'Gravenzande, The Netherlands in January 1995. The new variety was first asexually propagated by vegetative cuttings in March 1995, in s'Gravenzande, The Netherlands. Asexual reproduction through succeeding generations has established that the combination of characteristics as herein disclosed for the new cultivar are firmly fixed and retained through successive generations of asexual reproduction.

BRIEF DESCRIPTION OF THE DRAWINGS

The accompanying photographic illustrations show a specimen of the new cultivar grown under commercial conditions, with colors as nearly true as possible with illustrations of this type.

Sheet 1 shows the growth habit of the new plant.

Sheet 2 is a close-up illustration of the foliage.

DETAILED DESCRIPTION OF THE NEW VARIETY

'Eclipse' has not been observed under all possible environmental conditions. The phenotypic expression may vary with variations in environment such as temperature, light intensity, day length and cultural conditions, without, however, a change in the genotype of the plant.

The following observations and descriptions are of an 18 month old plant grown in a shade house covered with Saran providing 73% shade in Homestead, Fla., USA during the months of January 1998 through July of 2000. In this description, color references are to The Royal Horticultural Society (R.H.S.) Colour Chart. The color references are as accurate as possible as color depends to a degree on horticultural practices such as light level and fertilization rates.

In comparison with 'Midnight', 'Eclipse' has leaves that are more elliptic in shape with an exaggerated acuminate leaf tip. Additionally, 'Eclipse' has leaves with an exaggerated undulating leaf margin that is slightly crenate. The leaves from 'Eclipse' also have a high gloss on both topside and underside of the leaves. Internode length can be somewhat irregular and elongated when compared to the parent plant. The growth pattern of 'Eclipse' is less compact than that of its parent plant. When grown under the same environmental conditions, 'Midnight' will be more compact and upright with less crenate leaf margins that are less undulating than 'Eclipse'. Furthermore, 'Midnight' will not display gloss on the underside of the leaves. The leaf colors of the 'Eclipse' and the 'Midnight' varieties are nearly identical when grown under identical environmental conditions. The leaves of both 'Eclipse' and 'Midnight' are an attractive dark green that is almost blue-black without variegation.

Botanical: *Ficus benjamina* 'Eclipse'.

Parentage: Naturally-occurring mutation of *Ficus benjamina* 'Midnight'.

Propagation: By vegetative cuttings and other known asexual reproduction techniques.

PLANT

Form: Decurrent, somewhat weeping, upwardly branching, ascending irregularly and richly branching.

*Growth.*—a. Lateral branches tend to be at 30 to 45 degrees to the trunk, but somewhat weeping. b. Height Attained: 2 meters. c. Plant Spread: Approximately 180 cm. d. Trunk Diameter: 3.9 cm, as measured 15 cm above the soil line.

*Foliage.*—a. Size — about 30 mm wide by 40 mm wide and 55 to 70 mm long (to 1 leaf tip). b. Quantity — Multiple, numerous. c. Color — New foliage: upper side — near 137B; Underside — near 137C. Old foliage: Upper side — near 131A; Underside — near 139A to 139B; glossy. d. Shape — Elliptic with undulating crenate leaf margins with an acuminate leaf tip. e. Texture — Smooth and glabrous, leathery, glossy, underside smooth and glossy. f. Veination — Single mid-rib vein running from petiole to leaf tip, convex on underside, light green near 145D. g. Edge — Crenate, heavily undulated. h. Serration — None. i. Auricle — Absent. j. Petiole — Green, 138 A; about 13 mm long, diameter 1 mm. k. Disease Resistance — No particular claim is made to disease resistance. l. Rachis — None.

*Wood.*—a. New Shoots — Color near 197B; smooth. b. Old Wood — Color near 199A. To date and under conditions described herein, the new variety has not borne flowers or fruit. c. Node Spacing — About 25 to 40 mm. d. Preferred Growing Conditions — 20° C. to 32° C. e. Reproductive Organs — Not observed. f. Temperature range — From 2° C. to 40° C., with optimal growth occurring between 26° C. and 35° C.

I claim:

1. A new and distinct plant as herein described and illustrated.

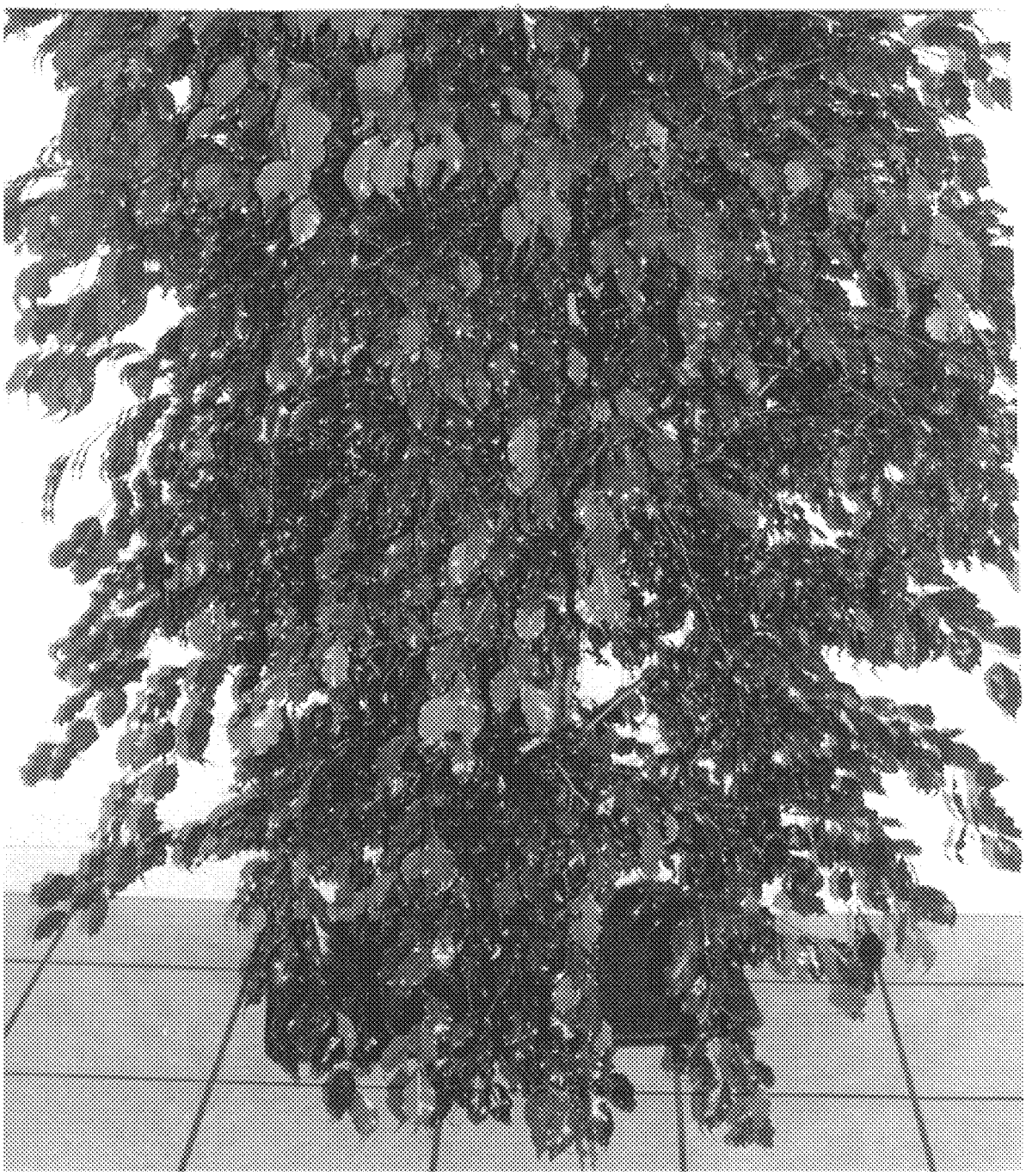

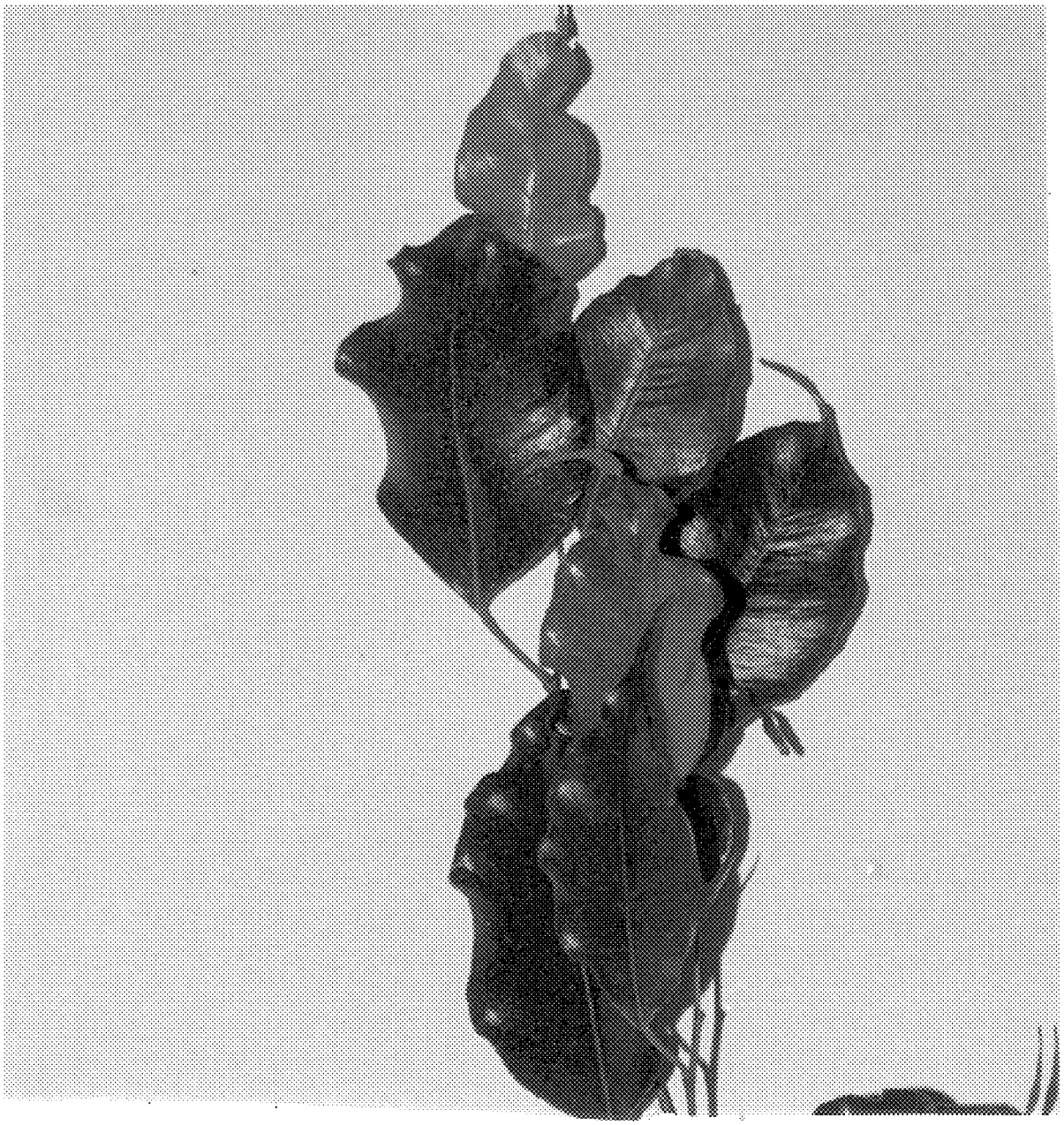

* * * * *